United States Patent

Chrzavzez née Taddei et al.

Patent Number: 6,117,636
Date of Patent: Sep. 12, 2000

[54] METHOD FOR DETECTING HEAT-RESISTANT MICRO-ORGANISMS CAPABLE OF CONTAMINATING CERTAIN FOOD PRODUCTS

[75] Inventors: Emmanuelle Chrzavzez née Taddei, Eckweesheim; Robert Aufrere, Sceaux, both of France

[73] Assignee: Ultra Propre Nutrition Industrie Recherche, Paris, France

[21] Appl. No.: 08/952,670

[22] PCT Filed: May 31, 1996

[86] PCT No.: PCT/FR96/00821

§ 371 Date: Mar. 9, 1998

§ 102(e) Date: Mar. 9, 1998

[87] PCT Pub. No.: WO96/38587

PCT Pub. Date: Dec. 5, 1996

[30] Foreign Application Priority Data

Jun. 2, 1995 [FR] France ................................. 95 06578

[51] Int. Cl.$^7$ .............................. C12Q 1/68; C12P 19/34; C07H 21/04
[52] U.S. Cl. ........................... 435/6; 435/91.2; 536/23.44
[58] Field of Search ..................... 435/6, 91.2; 536/24.33

[56] References Cited

U.S. PATENT DOCUMENTS 4,683,195  7/1987  Mullis et al. ................................. 435/6
5,324,632  6/1994  Weisburg et al. ............................ 435/6

FOREIGN PATENT DOCUMENTS 51-030139B  8/1976  Japan .

OTHER PUBLICATIONS

Nazar R.N. et al (Physiological and Molecular Plant Pathology (1991)39, 1–11 Potential use of PCR—Amplified Ribosomal Intergenic Sequences in the Detection and Differentiation of Verticillium with Pathogens, 1991.

Berbee, Mary L. et al. (Mycologia (1995) 87(2), 210–211 is *Penicillum monophyletic*? An Evaluation of Phylogeny in the Family Trichocomaceae from 185, 5.85 and Its Ribosomal DNA Sequence Data, 1995.

Beuhat, L.R. (Journal of Food Science (1986) 51(6), 1506–1510 Extraordinary Heat Resistance of *Talaromyces Flavus* and *Neosartorya fischeri* Ascospores in Fruit Products, 1986.

Stubbs, S. et al. (Letters in Applied Microbiology (1994)) 19, 268–272 Differentiation of the Spoilage Yeast *Zygosaccharomyces bailii* From Other Zygosaccharomyces species using 18S rDNA as Target for a Non–Radioactive ligase detection reaction, 1994.

James, S.A. et al. (Yeast 10:871–881) Genetic Interrelationship Among Species of the Genus Zygosaccharomyces as Revealed by Small—Sub Unit rRNA Gene Sequences.

*Primary Examiner*—Lisa B. Arthur
*Attorney, Agent, or Firm*—Foley & Lardner

[57] ABSTRACT

A method for detecting *Byssochlamys nivea*, *Neosartorya fischeri* and *Zygossaccharomyces bailii* micro-organisms by amplifying the genomic DNA of the targeted micro-organisms using as a primer a sequence contained on the internal transcript spacers (ITS) of the ribosomal unit, namely, for *Byssochlamys nivea*, on ITS1 corresponding to SEQ ID 1 and on ITS2 corresponding to SEQ ID 2; for *Neosartorya fischeri*, on ITS1 corresponding to SEQ ID 3, and on ITS2 corresponding to SEQ ID 4; and for *Zygosaccharomyes bailii*, on ITS1 corresponding to SEQ ID 5 and on ITS2 corresponding to SEQ ID 6.

12 Claims, No Drawings

METHOD FOR DETECTING HEAT-RESISTANT MICRO-ORGANISMS CAPABLE OF CONTAMINATING CERTAIN FOOD PRODUCTS

The instant application is a National Phase Application of International Application PCT/FR96/00821, filed May 31, 1996.

FIELD OF THE INVENTION

The present invention relates to a method for the rapid detection of heat-resistant eukaryotic microorganisms capable of contaminating certain products in the food sector, particularly fruit-based products.

BACKGROUND OF THE INVENTION

More particularly, the microorganisms studied are two filamentous fungi, *Byssochlamys nivea* and *Neosartorya fischeri* and a yeast, *Zygosaccharomyces bailii*.

These contaminants of food products can develop on the fruit-based products, giving them, particularly for *Byssochlamys nivea*, unpleasant notes of the plastic or antiseptic type; the growth of *Neosartorya fischeri* is responsible for spoilage and the appearance of mycotoxins, whereas as that of *Zygosaccharomyces bailii* causes a formation of gas.

These microorganisms particularly in the form of spores, exhibit a very high heat resistance which allows them to persist, even after conventional pasteurization treatments, which are applied in the food industry.

The existing tests allowing the detection of these microorganisms consist in altering the samples of a selective medium by taking advantage of, as a selection factor, the heat resistance of the filamentous fungi or the resistance of the yeast to certain preservatives conventionally used in the sector, such as benzoic acid. However, this type of detection involves cultures and, what is more, fairly long cultures, namely from several days to several weeks, which makes them practically unusable in the food sector since they could involve preserving the products, which may be contaminated, for a very long time.

The search is therefore underway for a detection test allowing the very rapid detection of these microorganisms, it being possible for the said test to be carried out in a few hours at the most, in order to find out rapidly if the sampled product can continue or otherwise to be treated in the subsequent stages.

DETAILED DESCRIPTION OF THE INVENTION

Accordingly, the present invention proposes a process allowing the detection of *Byssochlamys nivea, Neosartorya fischeri* and *Zygosaccharomyces bailii* by amplification of the genomic DNA of the targeted microorganisms using, as primers, a pair of sequences contained in the internal transcribed spacers (ITS) of the ribosomal unit:

for Byssochlamys nivea,
  on ITS1 corresponding to SEQ ID NO: 1,
  on ITS2 corresponding to SEQ ID NO: 2,
for *Neosartorya fischeri*,
  on ITS1 corresponding to SEQ ID NO: 3,
  on ITS2 corresponding to SEQ ID NO: 4,
for *Zygosaccharomyces bailii*
  on ITS1 corresponding to SEQ ID NO: 5,
  on ITS2 corresponding to SEQ ID NO: 6.

In the ITS1 and ITS2 sequences, there will be chosen more particularly,
  for *Byssochlamys nivea*, the sequence SEQ ID NO: 7 and SEQ ID NO: 8,
  for *Neosartorya fischeri* SEQ ID NO: 9 and SEQ ID NO: 10,
  for *Zygosaccharomyces bailii* SEQ ID NO: 11 and SEQ ID NO: 12.

Among the amplification methods which can be used, the so-called PCR (Polymerase Chain Reaction) method will be used more particularly.

The tests, reported in particular in the examples, show that these primers are perfectly discriminating and make it possible to distinguish between the desired microorganisms and the microorganisms, which are even very close, and related.

The present invention also relates to a process for detecting these microorganisms in food products, particularly with fruit-based food products and more particularly strawberry-based food products, in which the sample containing the fruits is pretreated so as to liberate and concentrate the spores or the cells, to reduce or suppress the action of the inhibitors of Taq Polymerase and to extract the DNA from the spores or cells.

More particularly, the samples containing solid products will be treated with a mixture of cellulase/hemicellulase so as to liquefy them and then filtered and centrifuged under conditions which make it possible to obtain a product containing the cells from which the DNA can be extracted.

Since the samples contain most often inhibitors of Taq Polymerase, it is necessary to provide for a stage which makes it possible to reduce the activity of the inhibitors, either by dilution, or by treatment of the sample with phenol-chloroform and precipitation with alcohol.

Although the present invention is more particularly intended for the food industry, it is evident that it can also be used to detect the microorganisms involved in other samples which might not have any relationship with the food industry.

Finally, the present invention relates to primers, as defined above, as well as detection kits using the said primers.

Other characteristics and advantages of the present invention will emerge on reading the examples below.

EXAMPLE 1

Procedure for Extraction of DNA and for Amplification

I) Starting with about 5 mm$^2$ of fungal mycelium, 10$^5$ fungal spores or 10$^6$ yeast cells:
  in a screw-top microtube (1.5 ml Eppendorf type), suspension of the microorganisms in 200 μl of 50 mM Tris buffer containing 20 mM EDTA, 0.8% SDS, pH 8.5, to which there are added 100 μl of glass beads (diameter 0.25–0.5 mm),
  vortex for 1 minute at maximum frequency,
  incubation of the mixture for 15 minutes at 100° C. (boiling water),
    for the treatment of the spores, the vortexing and the incubation are replaced with:
      freezing in liquid N$^2$, boiling 100° C. 5 minutes,
      refreezing in liquid N$^2$, boiling 100° C. 10 minutes,
  centrifugation 1 minute at 10,000 g (bench centrifuge),
  recovery of the supernatant
  10-fold dilution of the supernatant in water.
This diluted supernatant is used directly for the amplification.

(II) The amplification is carried out in a final volume of 25 µl containing 20 mM Tris-HCl pH 8.5, 16 mM $(NH_4)_2SO_4$, 2.5 mM $MgCl_2$, 150 µg/ml of bovine serum albumin, 0.2 µM of each dNTP and 100 µM of each of the primer oligonucleotides. Two units of Taq DNA polymerase (BioTaq, Bioprobe systems, France) are used by reaction. The amplification reaction is carried out in the Perkin Elmer 2400 thermocycler (Perkin Elmer Corp., U.S.A.) in the following manner:

for Zygosaccharomyces, Byssochlamys and Neosartoria
15 seconds at 94° C.
10 seconds at 58° C.
20 seconds at 72° C.

This cycle is repeated 30 times. It is followed by a 5 minute terminal extension at 72° C.

(III) The products obtained are visualized under UV after migration on an electrophoretic gel having the following composition: 1×TBE buffer, 1 µg/ml ethidium bromide, 0.8% agarose.

EXAMPLE 2

The results observed using the process according to the present invention on various strains close to the strains to be detected showing the excellent discrimination provided by the claimed sets of primers will be found below.

The primers used are:

SEQ ID 7 and 8 for *Byssochlamys nivea*,

SEQ ID 9 and 10 for *Neosartorya fischeri*,

SEQ ID 11 and 12 for *Zygosaccharomyces bailii*.

It should be noted that *A. fumigatus* responds to the probe because it is the asexual form of *N. fischeri*.

Primer oligonucleotides specific for *Neosartoria fischeri*

| Genus | Species | Strain | T ° C. hy. | PCR response |
|---|---|---|---|---|
| Aspergillus | floriformis | M 93 2663 | 57° C. | negative |
| Aspergillus | fumigatus | M 70 665 | 57° C. | positive |
| Aspergillus | fumigatus | M 88 2521 | 57° C. | positive |
| Byssochlamys | nivea | M 90 1496 | 57° C. | negative |
| Byssochlamys | nivea | M 93 2932 | 57° C. | negative |
| Emericella | nidulans | M 88 2519 | 57° C. | negative |
| Emericella | nidulans var. acristata | M 84 2558 | 57° C. | negative |
| Emericella | nidulans var. dentata | M 84 2556 | 57° C. | negative |
| Emericella | nidulans var. lata | M 68 1987 | 57° C. | negative |
| Emericella | nidulans var. shinulata | M 84 9557 | 57° C. | negative |
| Eupenicillium | brefeldianum | M 89 2573 | 57° C. | negative |
| Eurotium | amstelodami | M 50 142 | 57° C. | negative |
| Eurotium | amstelodami | M 88 2536 | 57° C. | negative |
| Eurotium | repens | M 66 2534 | 57° C. | negative |
| Mariannae | elegans | M 95 3777 | 57° C. | negative |
| Monascus | ruber | M 65 1079 | 57° C. | negative |
| Neosartoria | fennelliae | M 93 2982 | 57° C. | positive |
| Neosartoria | fennelliae | M 95 3781 | 57° C. | positive |
| Neosartoria | fennelliae | M 953780 | 57° C. | positive |
| Neosartoria | pseudofischeri | M 93 2986 | 57° C. | positive |
| Neosartoria | pseudofischeri | M 95 3784 | 57° C. | positive |
| Neosartorya | aurata | M 93 2980 | 57° C. | positive |
| Neosartorya | aureola | M 90 3623 | 57° C. | positive |
| Neosartorya | aureola | M 93 2981 | 57° C. | positive |
| Neosartorya | aureola | M 95 3785 | 57° C. | positive |
| Neosartorya | fennelliae | M 93 2983 | 57° C. | positive |
| Neosartorya | fischeri | M 90 2660 | 57° C. | positive |
| Neosartorya | fischeri var. fischeri | M 88 2482 | 57° C. | positive |

-continued

Primer oligonucleotides specific for *Neosartoria fischeri*

| Genus | Species | Strain | T ° C. hy. | PCR response |
|---|---|---|---|---|
| Neosartorya | fischeri var. fischeri | M 89 2707 | 57° C. | positive |
| Neosartorya | fischeri var. fischeri | M 90 3618 | 57° C. | positive |
| Neosartorya | fischeri var. fischeri | M 90 3619 | 57° C. | positive |
| Neosartorya | fischeri var. fischeri | M 90 3620 | 57° C. | positive |
| Neosartorya | fischeri var. fischeri | M 90 3621 | 57° C. | positive |
| Neosartorya | fischeri var. glabra | M 87 3513 | 57° C. | positive |
| Neosartorya | fischeri var. glabra | M 88 2480 | 57° C. | positive |
| Neosartorya | fischeri var. glabra | M 88 3577 | 57° C. | positive |
| Neosartorya | fischeri var. glabra | M 90 3622 | 57° C. | positive |
| Neosartorya | fischeri var. glabra | M 92 2891 | 57° C. | positive |
| Neosartorya | fischeri var. glabra | M 92 2925 | 57° C. | positive |
| Neosartorya | fischeri var - spinosa | M 88 2480 | 57° C. | positive |
| Neosartorya | fischeri var. spinosa | M 88 3574 | 57° C. | positive |
| Neosartorya | fischeri var. spinosa | M 90 2749 | 57° C. | positive |
| Neosartorya | fischeri var. spinosa | M 92 2862 | 57° C. | positive |
| Neosartorya | fischeri var. spinosa | M 92 2910 | 57° C. | positive |
| Neosartorya | fischeri var. spinosa | M 92 2924 | 57° C. | positive |
| Neosartorya | fischeri var. spinosa | M 93 2935 | 57° C. | positive |
| Neosartorya | hiratsukae | M 95 3782 | 57° C. | positive |
| Neosartorya | quadricincta | M 93 2984 | 57° C. | positive |
| Neosartorya | quadricincta | M 95 3786 | 57° C. | positive |
| Neosartorya | spathulata | M 93 2978 | 57° C. | positive |
| Neosartorya | spathulata | M 93 2979 | 57° C. | positive |
| Neosartorya | stramenia | M 93 2985 | 57° C. | positive |
| Neosartorya | tatenoi | M 95 3783 | 57° C. | positive |
| Paecilomyces | carneus | M 52 907 | 57° C. | negative |
| Paecilomyces | carneus | M 95 3776 | 57° C. | negative |
| Paecilomyces | elegans | M 79 1670 | 57° C. | negative |
| Paecilomyces | farinosus | M 75 3028 | 57° C. | negative |
| Paecilomyces | fumoso-roseus | M 52 597 | 57° C. | negative |
| Paecilomyces | inflatus | M 57 1387 | 57° C. | negative |
| Paecilomyces | javanicus | M 69 3302 | 57° C. | negative |
| Paecilomyces | javanicus | M 90 2684 | 57° C. | negative |
| Paecilomyces | lilacinus | M 2689 | 57° C. | negative |
| Paecilomyces | lilacinus | M 70 3099 | 57° C. | negative |
| Paecilomyces | marquandii | M 50 85 | 57° C. | negative |
| Paecilomyces | niphetodes | M 79 3238 | 57° C. | negative |
| Paecilomyces | niphetodes | M 95 3778 | 57° C. | negative |
| Paecilomyces | variotii | M 93 3701 | 57° C. | negative |
| Paecilomyces | zolemiae | M 93 3648 | 57° C. | negative |
| Penicillium | chrysogenum | M 47 673 | 57° C. | negative |
| Penicillium | islandicum | M 73 2233 | 57° C. | negative |
| Penicillium | islandicum | M 73 2233 | 57° C. | negative |
| Penicillium | purpurogenum | M 90 2600 | 57° C. | negative |
| Penicillium | variabile | M 78 3162 | 57° C. | negative |
| Penicillium | viridicatum | M 88 2485 | 57° C. | negative |
| Talaromyces | bacilliformis | M 88 1497 | 57° C. | negative |
| Talaromyces | bacilliformis | M 88 2511 | 57° C. | negative |
| Talaromyces | bacilliformis | M 90 1493 | 57° C. | negative |
| Talaromyces | bacilliformis | M 90 2646 | 57° C. | negative |
| Talaromyces | bacillisporus | M 88 2511 | 57° C. | negative |
| Talaromyces | flavus | M 83 1179 | 57° C. | negative |
| Talaromyces | flavus | M 88 2481 | 57° C. | negative |
| Talaromyces | flavus | M 89 1489 | 57° C. | negative |
| Talaromyces | flavus | M 93 2944 | 57° C. | negative |

-continued

Primer oligonucleotides specific for *Neosartoria fischeri*

| Genus | Species | Strain | T° C. hy. | PCR response |
|---|---|---|---|---|
| Talaromyces | *helicus* var. *helicus* | M 88 2510 | 57° C. | negative |
| Talaromyces | *luteus* | M 61 1858 | 57° C. | negative |
| Talaromyces | sp. | M 92 2885 | 57° C. | negative |
| Talaromyces | sp. | M 92 2887 | 57° C. | negative |
| Talaromyces | sp. | M 92 2888 | 57° C. | negative |
| Thermoascus | *crustaceus* | M 88 2540 | 57° C. | negative |

The strains obtained from the Paris National Museum of Natural History.

Primer Oligonucleotides specific for *Zygosaccharomyces bailii*

| Genus | Species | Strain | T° C. hy. | PCR response |
|---|---|---|---|---|
| Candida | *inconspicua* | M E10 | 50° C. | negative |
| Candida | *magnoliae* | M E14 | 50° C. | negative |
| Candida | *mogii* | M 95 3795 | 55° C. | negative |
| Clavispora | *lusitaniae* | M E9 | 50° C. | negative |
| Clavispora | *lusitaniae* | SIAS | 58° C. | negative |
| Cytofilobasidium | | ME13 | 50° C. | negative |
| Debaryomyces | *hansenii* | SIAS | 58° C. | negative |
| Debaryomyces | *hansenii* | M E18 | 50° C. | negative |
| Hyphopichia | | M E6 | 50° C. | negative |
| Kluyveromyces | *marxianus* var. *lactis* | M 95 3788 | 55° C. | negative |
| Kluyveromyces | *marxianus* var. *lactis* | M 95 3789 | 55° C. | negative |
| Kluyveromyces | *marxianus* var. *marxianus* | M 95 3790 | 55° C. | negative |
| Kluyveromyces | *marxianus* var. *marxianus* | M 95 3791 | 55° C. | negative |
| Kluyveromyces | var. *lactis* | P 8 | 57° C. | negative |
| Moniliella | | M E2 | 50° C. | negative |
| Pichia | *anomala* | M E12 | 50° C. | negative |
| Pichia | *anomala* | SIAS | 58° C. | negative |
| Pichia | *fermentans* | SIAS | 58° C. | negative |
| Pichia | *guilliermondii* | SIAS | 58° C. | negative |
| Pichia | *guilliermondii* | M E17 | 50° C. | negative |
| Pichia | *pastoris* | M 95 3792 | 55° C. | negative |
| Pichia | *pastoris* | M 95 3793 | 55° C. | negative |
| Rhodoturola | *mucilaginosa* | M E15 | 50° C. | negative |
| Saccharomyces | *bayanus* | M 95 3796 | 55° C. | negative |
| Saccharomyces | *bayanus* | P 562 | 57° C. | negative |
| Saccharomyces | *bayanus* | P 563 | 57° C. | negative |
| Saccharomyces | *capsularis* | M 95 3807 | 55° C. | negative |
| Saccharomyces | *cerevisiae* | H 5035 | 57° C. | negative |
| Saccharomyces | *cerevisiae* | H 5090 | 57° C. | negative |
| Saccharomyces | *cerevisiae* | H 5130 | 57° C. | negative |
| Saccharomyces | *cerevisiae* | H 5160 | 57° C. | negative |
| Saccharomyces | *cerevisiae* | H 5200 | 57° C. | negative |
| Saccharomyces | *cerevisiae* | H 5334 | 57° C. | negative |
| Saccharomyces | *cerevisiae* | M E16 | 50° C. | negative |
| Saccharomyces | *cerevisiae* | P 1 | 57° C. | negative |
| Saccharomyces | *cerevisiae* | P 575 | 57° C. | negative |
| Saccharomyces | *cerevisiae* | SIAS | 58° C. | negative |
| Saccharomyces | *exiguus* | M 95 3797 | 55° C. | negative |
| Saccharomyces | *kluyveri* | M 95 3798 | 55° C. | negative |
| Saccharomyces | *ludwigii* | M 95 3806 | 55° C. | negative |
| Saccharomyces | *servazii* | M 95 3799 | 55° C. | negative |
| Saccharomyces | *stellatus* | M 95 3803 | 55° C. | negative |
| Saccharomyces | *stellatus* | M 95 3804 | 55° C. | negative |
| Saccharomyces | *unisporus* | M 95 3805 | 55° C. | negative |
| Schyzosaccharomyces | *pombe* | H 5096 | 57° C. | negative |
| Osmophilic strain | | H 11 077 | 57° C. | negative |
| Osmophilic strain | | H 37 080 | 57° C. | negative |
| Torulaspora | *delbruckii* | M 95 3794 | 55° C. | negative |
| Torulaspora | *delbruckii* | P L121 | 57° C. | negative |

Primer Oligonucleotides specific for Zygosaccharomyces bailii

| Genus | Species | Strain | T°C. hy. | PCR response |
|---|---|---|---|---|
| Torulaspora | delbruckii | SIAS | 58° C. | negative |
| Trichosporum | capitatum | SIAS | 50° C. | negative |
| Zygosaccharomyces | bailii | M 90 2638 | 58° C. | positive |
| Zygosaccharomyces | bailii | M 90 2639 | 55° C. | positive |
| Zygosaccharomyces | bailii | M 92 2895 | 55° C. | positive |
| Zygosaccharomyces | bailii | M 92 2896 | 55° C. | positive |
| Zygosaccharomyces | bailii | M 92 2897 | 58° C. | positive |
| Zygosaccharomyces | bailii | M 92 2899 | 58° C. | positive |
| Zygosaccharomyces | bailii | M 92 2900 | 58° C. | positive |
| Zygosaccharomyces | bailii | M 92 2901 | 55° C. | positive |
| Zygosaccharomyces | bailii | M 92 2902 | 55° C. | positive |
| Zygosaccharomyces | bailii | M 92 2903 | 58° C. | positive |
| Zygosaccharomyces | bailii | M 92 2904 | 55° C. | positive |
| Zygosaccharomyces | bailii | M 92 2905 | 55° C. | positive |
| Zygosaccharomyces | bailii | M 92 2906 | 55° C. | positive |
| Zygosaccharomyces | bailii | M 92 2907 | 55° C. | positive |
| Zygosaccharomyces | bailii | M 92 2908 | 58° C. | positive |
| Zygosaccharomyces | bailii | M 92 2909 | 58° C. | positive |
| Zygosaccharomyces | bailii | M 92 2911 | 55° C. | positive |
| Zygosaccharomyces | bailii | M 92 2912 | 58° C. | positive |
| Zygosaccharomyces | bailii | M 92 2913 | 58° C. | positive |
| Zygosaccharomyces | bailii | M 92 2914 | 55° C. | positive |
| Zygosaccharomyces | bailii | M 92 2915 | 58° C. | positive |
| Zygosaccharomyces | bailii | M 92 2916 | 55° C. | positive |
| Zygosaccharomyces | bailii | M 92 2917 | 58° C. | positive |
| Zygosaccharomyces | bailii | M 92 2918 | 58° C. | positive |
| Zygosaccharomyces | bailii | M 92 2920 | 55° C. | positive |
| Zygosaccharomyces | bailii | M 92 2921 | 55° C. | positive |
| Zygosaccharomyces | bailii | M 92 2922 | 58° C. | positive |
| Zygosaccharomyces | bailii | M 92 2923 | 58° C. | positive |
| Zygosaccharomyces | bailii | M E11 | 55° C. | positive |
| Zygosaccharomyces | bailii | PL443 | 58° C. | positive |
| Zygosaccharomyces | bisporus | DBVPG 6382 | 58° C. | negative |
| Zygosaccharomyces | cidri | DBVPG 6385 | 55° C. | negative |
| Zygosaccharomyces | fermentati | DBVPG 6297 | 55° C. | negative |
| Zygosaccharomyces | florentinus | DBVPG 6186 | 55° C. | negative |
| Zygosaccharomyces | microellipsoides | DBVPG 6188 | 55° C. | negative |
| Zygosaccharomyces | mrakii | DBVPG 6289 | 55° C. | negative |
| Zygosaccharomyces | rouxii | MJCL 30008 | 55° C. | negative |
| Zygosaccharomyces | rouxii | SIAS | 58° C. | negative |

SOURCE OF THE STRAINS
DEVPG: Department of Plant Biology, Perugia (Italy)
H: Heudebert Company
M: Paris National Museum of Natural History
MUCL: Fungus Culture Collection of the Catholic University of Louvains
P: Pernod-Ricard Company
SIAS: Company SIAS France Source of the Strains DBVPG: Department of Plant Biology, Perugia (Italy)
H: Heudebert Company
M: Paris National Museum of Natural History
MUCL: Fungus Culture Collection of the Catholic University of Louvains
P: Pernod-Ricard Company
SIAS: Company SIAS France

We claim:

1. A method for detecting the presence or absence of *Byssochlamys nivea, Neosartorya fischeri* or *Zygosaccharomyces bailii* in a sample, comprising amplifying the DNA in the sample using a primer composition which specifically hybridizes to the ITS regions of SEQ ID Nos. 1–6, or which specifically hybridizes to the complement of SEQ ID Nos. 1–6, to produce amplified fragments and detecting the presence or absence of the amplified fragments to thereby detect the presence of *Byssochlamys nivea, Neosartorya fischeri* or *Zygosaccharomyces bailii*.

2. The method of claim 1, wherein the primer composition is a primer composition comprising SEQ ID Nos. 7–12.

3. The process according to claim 1, wherein said amplifying is carried out by the PCR method.

4. The process according to claim 1, wherein said microorganisms are detected in food products.

5. The process according to claim 4, wherein said food products are fruit-based products.

6. The process according to claim 5, wherein a sample containing said fruit-based products is pretreated prior to step (i) so as to liberate and concentrate the spores or the cells, to reduce or suppress the action of the inhibitors of Taq Polymerase, and to extract the DNA from said spores or cells.

7. The process according to claim 5, wherein said fruit-based products are strawberry-based food products.

8. The process according to claim 5, wherein samples containing said fruit-based products are treated with a mixture of cellulase/hemicellulase so as to liquefy them and then filtered and centrifuged under conditions which make it possible to obtain a product containing the cells from which the DNA can be extracted.

9. A primer composition comprising SEQ ID Nos. 7–12.

10. A kit comprising SEQ ID Nos. 7–12.

11. A primer composition comprising primers which specifically hybridize to the ITS regions of SEQ ID Nos. 1–6 or to the complementary sequences thereof.

12. A kit comprising a primer composition according to claim 7.

* * * * *

```
                         SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
        (A) LENGTH: 186 base pairs
        (B) TYPE: nucleic acid
        (C) STRANDEDNESS: single
```

(D) TOPOLOGY: linear (ii) MOLECULE TYPE: DNA (genomic)

(xi) SEQUENCE DESCRIPTION: SEQ ID NO:1:

CCGAGTGCGG GTCCCTCGTG CCCCAACCTC AACCCGTGT TGACCGACAC CTGTTGCTTC    60

GGCGGGCCCG CCCATGGGCT CCCGCCCGGC CGCCGGGGGG CCTCGTCGCC CCCGGGCCCG   120

CCGCCCGCCG AAGACCCCTC GAACGCTGCC TTGAAGGTTG CCGTCTGAGT ATAAAATCAA   180

TCGTTA                                                             186

(2) INFORMATION FOR SEQ ID NO:2:

(i) SEQUENCE CHARACTERISTICS:
        (A) LENGTH: 187 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

GCTAACCCTC CAGCCCGGCT GGTGTGTTGG GCCGCCGTCC CCTCCGGGGG ACGGGCCCGA    60

AAGGCAGCGG CGGCGCCGTC CGGTCCTCGA GCGTATGGGG CTTTGTCACA CGCTCTGGTA   120

GGCCCGGCCG GCTTGCTGGC AAACGACCTC ACGGTCACCT AACTTCTCTC TTAGGTTGAC   180

CTCGGAT                                                            187

(2) INFORMATION FOR SEQ ID NO:3:

(i) SEQUENCE CHARACTERISTICS:
        (A) LENGTH: 183 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

CCGAGTGAGG GCCTCTGGGT CCAACTTCCC ACCCGTGTCT ATCGTACCTT GTTGCTTCGG    60

CGGGCCCGCC GTTTCGACGG CCGCCGGGGA GGCCTCGCGC CCCCGGGCCC GCGCCCGCCG   120

AAGACCCCAA CATGAACGCT GTTCTGAAAG TATGCAGTCT GAGTTGATTA TCATAATCAG   180

TTA                                                                183

(2) INFORMATION FOR SEQ ID NO:4:

(i) SEQUENCE CHARACTERISTICS:
        (A) LENGTH: 176 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

GCTGCCCTCA GGCACGGCTT GTGTGTTGGG CGTCCCCTCT CCCGGGAACG GGCCCGAAAG    60

GCAGCGGCGG CACCGCGTCC GGTCCTCGAG CGTATGGGGC TTTGTCACCC GCTCTGTAGG   120

CCCGGCCGGC GCCAGCCGAC ACCCAACTTT ATTTCTAAGG TTGACCTCGG ATCAGG       176

(2) INFORMATION FOR SEQ ID NO:5:

(i) SEQUENCE CHARACTERISTICS:

(A) LENGTH: 279 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

TAGAAAAATT TCTGATTGAC GAGTCTGGAG CAGTTGTGTT CTTTCTGTTT TTTTTAAGGC      60

CTGCGCTTAA TTGCCGTCTA GAGCGGAGGG AGTTAAGCAT AGTTGCCTTT GGCTTTCAAT     120

TTACACACAG TGGAGTTTCT ACTTTTTTTA TTCTTCTTTG GGAGGATGGG TTCGTCCCGC     180

TCCCAGAGGT AAACACAAAC AATTTTTTTT ATTTTATTTT ATTTTATTAT TATAATAATA     240

ATAATACAGT CAAAACGAAT ACTAAAAAAA AAATATTCA                            279

(2) INFORMATION FOR SEQ ID NO:6:

(i) SEQUENCE CHARACTERISTICS:
        (A) LENGTH: 237 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

CCTTCTCAAA CATTCGTGTT TGGTAGTGAG TGATACTCTG TTTTATATTT GGGTTAACTT      60

GAAATTGCAA GCCTTTTGGG ACGCGTGTGG GTGAGTTTTA GGCCGGAAAC GTCTTGCTCT     120

CCTCTTTCCT AACCAAATGT CGTATTAGGT TTTACCGACT CCGACAGACG GGACTAGGAG     180

ATTGGGTGAG TGATAGCAAT ATCGAGCTCT GCCTAATTTT TTTTTTTGCG CGCCTTG       237

(2) INFORMATION FOR SEQ ID NO:7:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

GGTTGCCGTC TGAGTATAAA ATCAA                                           25

(2) INFORMATION FOR SEQ ID NO:8:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

GAAGTTAGGT GACCGTGAGG TCGTT                                           25

(2) INFORMATION FOR SEQ ID NO:9:

(i) SEQUENCE CHARACTERISTICS:
        (A) LENGTH: 25 base pairs
        (B) TYPE: nucleic acid
        (C) STRANDEDNESS: single
        (D) TOPOLOGY: linear -continued (ii) MOLECULE TYPE: DNA (genomic)

(xi) SEQUENCE DESCRIPTION: SEQ ID NO:9:

AAGACCCCAA CATGAACGCT GTTCT                                        25

(2) INFORMATION FOR SEQ ID NO:10:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:10:

TCCGAGGTCA ACCTTAGAAA TAAAGTT                                      27

(2) INFORMATION FOR SEQ ID NO:11:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:11:

TAGAGCGGAG GGAGTTAAGC ATAGT                                        25

(2) INFORMATION FOR SEQ ID NO:12:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:12:

TGGTTAGGAA AGAGGAGAGC AAGAC                                        25